United States Patent
Andersson et al.

(10) Patent No.: US 6,790,998 B2
(45) Date of Patent: Sep. 14, 2004

(54) PHENYL INDEN-1-ONE COMPOUNDS

(75) Inventors: Pher G. Andersson, Uppsala (SE); Christian Hedberg, Uppsala (SE)

(73) Assignee: Pharmacia AB, Stockholm (SE)

( * ) Notice: Subject to any disclaimer, the term of this patent is extended or adjusted under 35 U.S.C. 154(b) by 81 days.

(21) Appl. No.: 10/402,671

(22) Filed: Mar. 28, 2003

(65) Prior Publication Data

US 2003/0191348 A1 Oct. 9, 2003

Related U.S. Application Data

(62) Division of application No. 09/919,401, filed on Jul. 31, 2001, now Pat. No. 6,566,537, which is a division of application No. 09/748,042, filed on Dec. 22, 2000, now Pat. No. 6,310,248.
(60) Provisional application No. 60/177,439, filed on Jan. 21, 2000.

(30) Foreign Application Priority Data

Dec. 30, 1999 (SE) ................................. 9904850

(51) Int. Cl.$^7$ ............................................. C07C 49/537

(52) U.S. Cl. ....................................................... 568/327

(58) Field of Search ......................................... 568/327

(56) References Cited

U.S. PATENT DOCUMENTS 6,566,537 B2 * 5/2003 Anderson et al. ............ 549/283

FOREIGN PATENT DOCUMENTS

| WO | WO8906644 | 7/1989 |
|---|---|---|
| WO | WO97107330 | 5/1997 |
| WO | WO9829402 | 7/1998 |

OTHER PUBLICATIONS

Clark, et al., A Highly Enantioselective Conjugate Reduction of 3–Arylinden–1–ones Using Bakers' Yeast for the Preparation of (S)–3–Arylindan–1–ones†, *Organic Letters*, vol. 1, No. 11, pp. 1839–1842 (1999).

Meyers et al., An Asymmetric Synthesis of 5–Methoxy–3–Substituted Acids and Their Related Lactones in High Enantiomeric Purity, *Tetrahedron Letters*, No. 23, pp. 1947–1950 (1976).

Andersson, et al., Asymmetric Total Synthesis of (+)–Tolterodine, a New Muscarinic Receptor Antagonist, via Copper–Assisted Asymmetric Conjugate Addition of Aryl Grignard Reagents to 3–Phenyl–prop–2–enoyl–oxazolidinones, *Journal of Organic Chemistry*, vol. 63, pp. 8067–8070 (1998).

Nielsen, et al., Antileishmanial Chalcones: Statistical Design, Synthesis, and Three–Dimensional Quantitative Structure–Activity Relationship Analysis, *Journal of Medical Chemistry*, vol. 41, pp. 4819–4832 (1998).

Batt, et al., 2'–Substituted Chalcone Derivatives as Inhibitors of Interleukin–1 Biosynthesis, *Journal of Medical Chemistry*, vol. 36, pp. 1434–1442, (1993).

Sogawa, et al., 3,4–Dihydroxychalcones as Potent 5–Lkpoxygenase and Cyclooxygenases Inhibitors, *Journal of Medical Chemistry*, vol. 36, pp. 3904–3909 (1993).

Joshi, et al., Facile Synthesis of Fluorine Containing 1,3, 5–Triarylpyrazoles and 3,5–Diarylisoxazoles, *Journal Indian Chem. Soc.*, vol. LXV, pp. 773–777 (1988).

Hsu, et al., Synthesis of Sulfamylchalcones, *Journal Chin. Chem. Soc.*, (Taipei), 16(3), 91–6, p. 1 (1969) (English Abstract).

Manimaran et al, *Indian Journal Chem.*, Sect. B, 18VB(4), 324–30 (1979), abs.

* cited by examiner

Primary Examiner—Brian Davis
(74) Attorney, Agent, or Firm—Dinsmore & Shohl LLP

(57) ABSTRACT

The invention relates to a process for the enantioselective preparation of tolterodine and analogues and salts thereof comprises the steps of:

a) enantioselectively reducing the carbonyl function in a compound of formula (II):

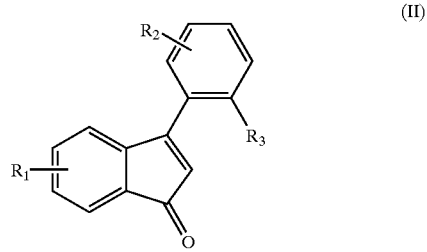

wherein $R_1$, $R_2$ and $R_3$ independently of each other are hydrogen, methyl, methoxy, hydroxy, hydroxymethyl, carbamoyl, sulphamoyl or halogen, to form an enantiomerically enriched compound of formula (IIIa) or (IIIb):

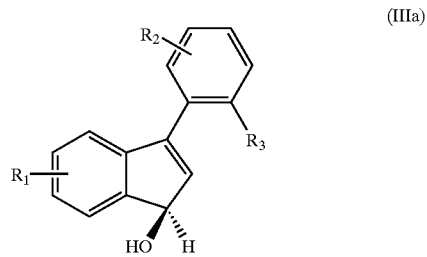

-continued

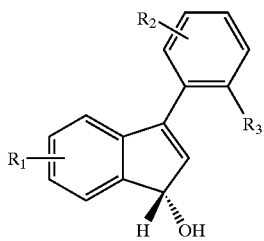
(IIIb)

wherein $R_1$, $R_2$ and $R_3$ are as defined above;

b) subjecting the compound of formula (IIIa) or (IIIb) to a sigmatropic rearrangement to form a corresponding enantiomerically enriched compound of formula (IVa) or (IVb):

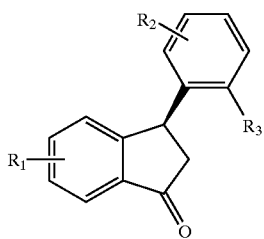
(IVa)

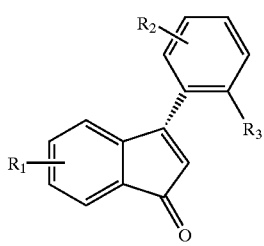
(IVb)

wherein $R_1$, $R_2$ and $R_3$ are as defined above;

c) subjecting the compound of formula (IVa) or (IVb) to a Baeyer-Villiger oxidation to form a corresponding enantiomerically enriched compound of the general formula (Va) or (Vb).

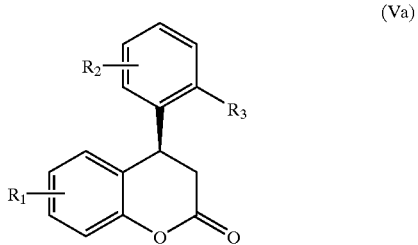
(Va)

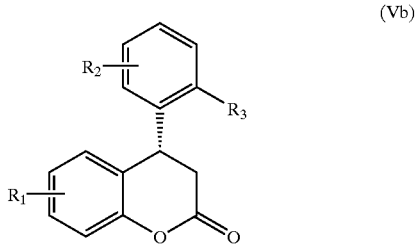
(Vb)

wherein $R_1$, $R_2$ and $R_3$ are as defined above;

d) converting the compound of formula (Va) or (Vb) to form the corresponding enantiometrically enriched compound of tolterodine or analogue, and e) optionally converting a compound obtained in base form to a salt thereof, or converting a salt form to the free base.

The invention also relates to novel starting materials and intermediates used in the process.

4 Claims, No Drawings

PHENYL INDEN-1-ONE COMPOUNDS

RELATED APPLICATIONS

The present application is a divisional of U.S. application Ser. No. 09/919,401 filed Jul. 31, 2001, now U.S. Pat. No. 6,566,537, which in turn was a divisional of U.S. application Ser. No. 09/748,042 filed Dec. 22, 2000, now U.S. Pat. No. 6,310,248, which in turn claims priority under 35 U.S.C. §119 of U.S. Provisional Application Serial No. 60/177,439 filed Jan. 21, 2000.

FIELD OF THE INVENTION

The present invention relates to a novel process of preparing tolterodine and analogues thereof, as well as to novel intermediates prepared in the process.

BACKGROUND OF THE INVENTION

Tolterodine, i.e. (R)-N,N-diisopropyl-3-(2-hydroxy-5-methylphenyl)-3-phenylpropanamine, is useful for treating urinary incontinence. The major, active metabolite of tolterodine, i.e. (R)-N,N-diisopropyl-3-(2-hydroxy-5-hydroxymethylphenyl)-3-phenylpropanamine, contributes significantly to the therapeutic effect of tolterodine. Tolterodine and analogues thereof, including the corresponding (S)-enantiomer, as well as processes for the preparation thereof are disclosed in U.S. Pat. No. 5,382,600. The active metabolite and analogues are disclosed in U.S. Pat. No. 5,559,269. The (S)-enantiomer and its use in the treatment of urinary and gastrointestinal disorders is further described in WO 98/03067.

One of the processes described in U.S. Pat. No. 5,382,600 comprises the steps of preparing the lactone 3,4-dihydro-6-methyl-4-phenyl-2H-benzopyran-2-one, reductively ring-opening the lactone to prepare the corresponding alcohol, reacting the alcohol with isopropylamine, and resolving the racemate formed to isolate tolterodine.

U.S. Pat. No. 5,922,914 discloses a modified process for preparing tolterodine by reducing the above-mentioned lactone to the corresponding alcohol, 3,4-dihydro-6-methyl-4-phenyl-2H-benzopyran-2-ol, reductively aminating the alcohol, and resolving the racemate formed to isolate tolterodine.

While the above prior art methods thus produce a racemate which has to be resolved to obtain the desired tolterodine enantiomer, Andersson, Pher G. et al., J. Org. Chem. 1998, 63, 8067–8070 discloses an enantioselective synthesis of tolterodine which obviates the need of the enantiomer separation step. This method comprises a copper bromide catalyzed asymmetric addition of 2-methoxy-5-methylphenylmagnesium bromide to a 3-phenyl-prop-2-enoyl-oxazolidinone to produce the (5S)-phenyl-(3R)-(2-benzyloxy-5-methylphenyl)-3-phenylpropanoyl-2-oxazolidinone, hydrolyzation of the oxazolidinone to the corresponding propanoic acid, reaction with diisopropylamine to form the amide, and reduction of the amide to tolterodine.

SUMMARY OF THE INVENTION

The present invention provides an alternate enantioselective synthesis of tolterodine which is more convenient to perform than the prior art method outlined above and which gives a final product of high enantiomeric purity. A key step of the present method is the preparation of the above-mentioned lactone, 3,4-dihydro-6-methyl-4-phenyl-2H-benzopyran-2-one (also referred to as 6-methyl-4-phenyl-chroman-2-one), in an enantiomerically enriched form by enantioselective reactions.

Thus, in a first aspect the present invention provides a process for the enantioselective preparation of a compound of the general formula (Ia) or (Ib):

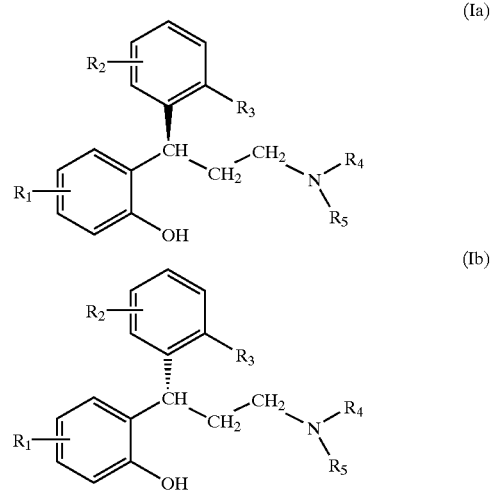

wherein $R_1$, $R_2$ and $R_3$ independently of each other are hydrogen, methyl, methoxy, hydroxy, hydroxymethyl, carbamoyl, sulphamoyl or halogen, and $R_4$ and $R_5$ independently of each other are $C_{1-6}$-alkyl, or a salt thereof, which process comprises the steps of:

a) enantioselectively reducing the carbonyl function in a compound of formula (II):

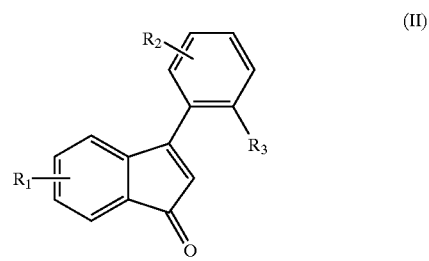

wherein $R_1$, $R_2$ and $R_3$ are as defined above, to form an enantiomerically enriched compound of formula (IIIa) or (IIIb):

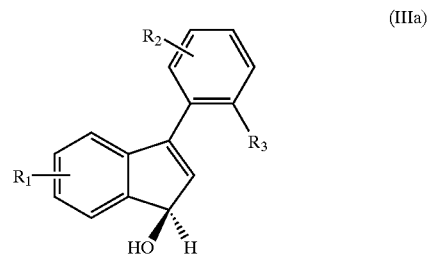

-continued

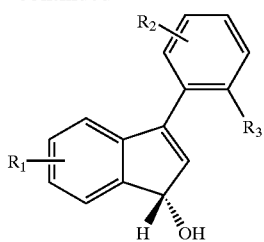
(IIIb)

wherein $R_1$, $R_2$ and $R_3$ are as defined above, or a salt thereof, b) subjecting the compound of formula (IIIa) or (IIIb) to a sigmatropic rearrangement to form a corresponding enantiomerically enriched compound of formula (IVa) or (IVb):

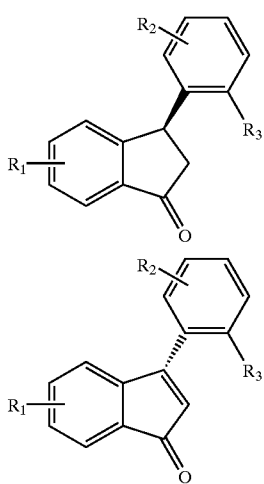
(IVa)

(IVb)

wherein $R_1$, $R_2$ and $R_3$ are as defined above, or a salt thereof;

c) subjecting the compound of formula (IVa) or (IVb) to a Baeyer-Villiger oxidation to form a corresponding enantiomerically enriched compound of the general formula (Va) or (Vb):

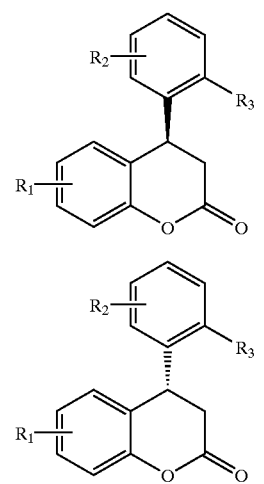
(Va)

(Vb)

wherein $R_1$, $R_2$ and $R_3$ are as defined above or a salt thereof;

d) converting the compound of formula (Va) or (Vb) to form the corresponding enantiometrically enriched compound of formula (Ia) or (Ib), or a salt thereof; and e) optionally converting a compound of formula (Ia) or (Ib) in base form to a salt thereof, or converting a salt form to the free base.

In one embodiment of the first aspect of the invention, step d) comprises:

d1) reacting the compound of formula (Va) or (Vb) with an amine of the general formula (VI):

(VI)

wherein $R_4$ and $R_5$ are as defined above, to form a corresponding enantiomerically enriched compound of the general formula (VIIa) or (VIIb):

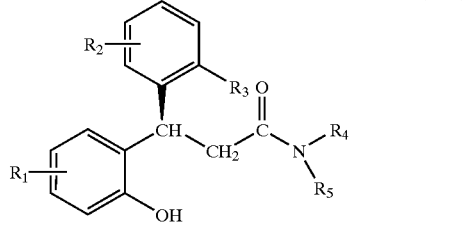
(VIIa)

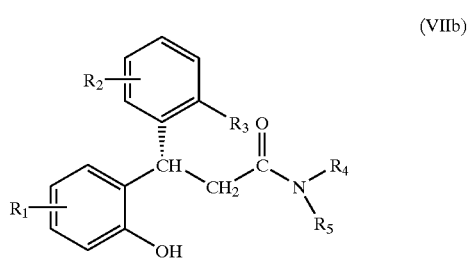
(VIIb)

wherein $R_1$, $R_2$, $R_3$, $R_4$ and $R_5$ are as defined above; and d2) reducing the carbonyl function in the compound of formula (VIIa) or (VIIb) to form the corresponding enantiomerically enriched compound of formula (Ia) or (Ib).

Optionally, steps d1) and d2) are performed simultaneously in a single step.

In an alternative embodiment, step d) comprises:

d1') reducing the compound of formula (Va) or (Vb) to form a corresponding enantiomerically enriched hydroxy compound of the general formula (VIIIa) or (VIIIb):

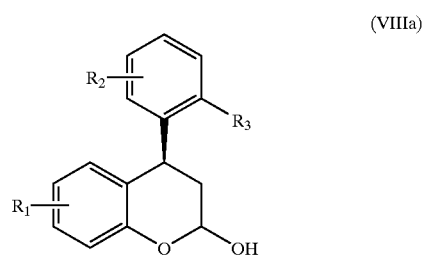
(VIIIa)

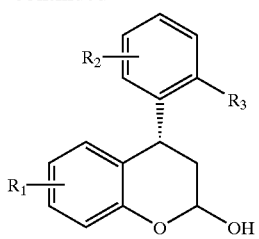
(VIIIb)

wherein $R_1$, $R_2$ and $R_3$ are as defined in claim 1; and d2') reductively aminating the hydroxy compound of formula (VIIIa) or (VIIIb) with the amine of formula (VI) to form the corresponding enantiomerically enriched compound of formula (Ia) or (Ib).

In second aspect, the present invention provides a process for the enantioselective preparation of a compound of the general formula (Va) or (Vb):

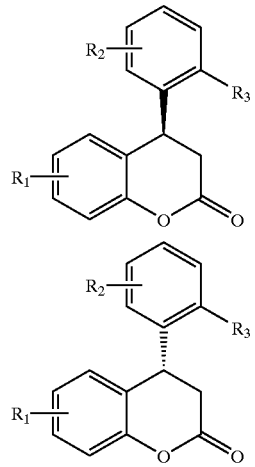
(Va)
(Vb)

wherein $R_1$, $R_2$ and $R_3$ are as defined above, or a salt thereof, which process comprises the steps of:

a) enantioselectively reducing the carbonyl function in a compound of formula (II):

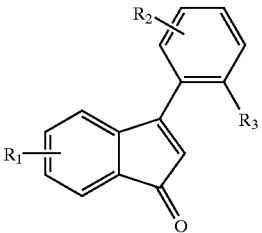
(II)

wherein $R_1$, $R_2$ and $R_3$ are as defined above, or a salt thereof, to form an enantiomerically enriched compound of formula (IIIa) or (IIIb):

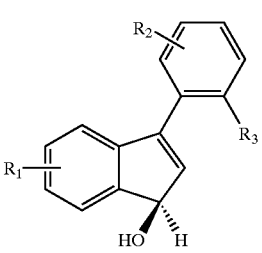
(IIIa)

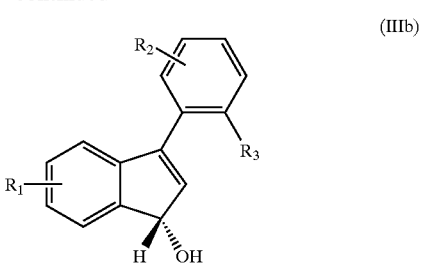
(IIIb)

wherein $R_1$, $R_2$ and $R_3$ are as defined above, or a salt thereof;

b) subjecting the compound of formula (IIIa) or (IIIb) to a sigmatropic rearrangement to form a corresponding enantiomerically enriched compound of formula (IVa) or (IVb):

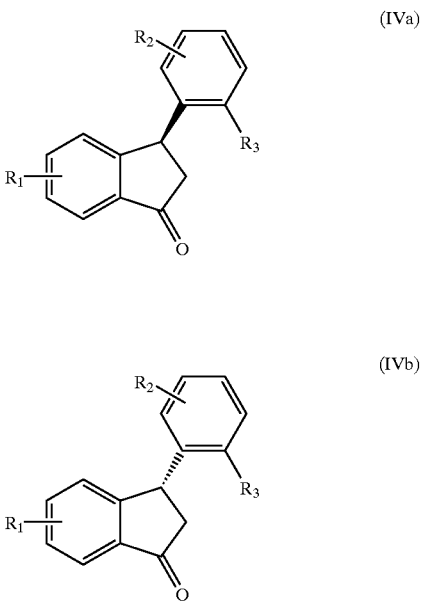
(IVa)
(IVb)

wherein $R_1$, $R_2$ and $R_3$ are as defined above, or a salt thereof; and c) subjecting the compound of formula (IVa) or (IVb) to a Baeyer-Villiger oxidation to form the corresponding enantiomerically enriched compound of the general formula (Va) or (Vb), or salt thereof.

The compound of formula (II) may be prepared by subjecting a compound of the general formula (IX):

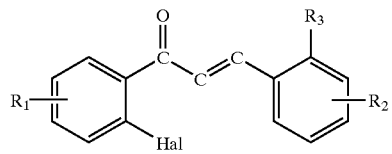
(IX)

wherein $R_1$, $R_2$, and $R_3$ are as defined in claim 1, and Hal is halogen (preferably bromine), or a salt thereof, to a reductive ring closure reaction.

The compound of formula (IX) may be prepared by reacting a compound of the general formula (X):

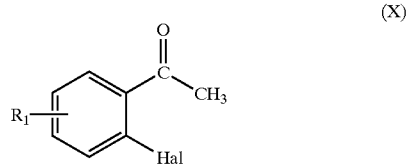

wherein $R_1$ and Hal are as defined above, with a compound of the general formula (XI):

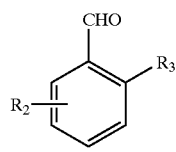

wherein $R_2$ and $R_3$ are as defined above.

Preferably, compounds of formula Ia or Ib are prepared in which $R_1$ is methyl or hydroxymethyl in 5-position, $R_2$ and $R_3$ are hydrogen, and $R_4$ and $R_5$ are both iso-propyl.

In a third aspect, the present invention provides novel compounds of the above of the formulae (II), (IIa), (IIIb), (IVa), (IVb), (Va), (Vb), and (IX) as defined above and wherein $R_1$ is methyl or hydroxymethyl in 5-position, or for (Va) and (Vb), in 6-position, and $R_2$ and $R_3$ are hydrogen and compounds of the formulae (IX) wherein $R_1$ is methyl or hydroxymethyl in 5-position or 4-position, $R_2$ and $R_3$ are hydrogen and halogen is Br, I or F.

DETAILED DESCRIPTION OF THE INVENTION

A basic concept behind the present invention is the enantioselective reduction of the compound of formula (II) to a compound of formula (IIIa) or (IIIb) in enantiomerically enriched form, which is then rearranged to form the lactone (Va) or (Vb). The respective lactone enantiomers may then be reacted further to tolterodine by methods known per se in the art, e.g. as described in the above-mentioned U.S. Pat. No. 5,382,600 and U.S. Pat. No. 5,922,914.

The enantioselective reduction of the compound (II) to a compound of formula (IIIa) or (IIIb) may be performed in an organic solvent with a variety of reducing agents and reaction conditions as are known per se in the art for enantioselective reduction of carbonyl groups. Such methods are described in, for example, Houben-Weyl, Stereoselective Synthesis, Ed: Günter Helmchen et al., Vol. 7, Chapter 2.3, Thime, Stuttgart-New York 1996. Preferably, the reaction is carried out at from about 0° C. to about room temperature. An exemplary method includes the use of a chiral catalyst, such as (R)- or (S)-MeCBS (3,3-diphenyl-1-methyltetrahydro-1H,3H-pyrrolo-[1,2-c][1.3.2] oxazaborole) which is commercially available, a borane complex and a base. The stereochemistry can be directed by using either the R or S enantiomer of the MeCBS oxazaborolidine catalyst in the asymmetric borane reduction of the compound (II). The reduction of a similar substrate is described in, for example, WO 97/17341. The enantioselectivity of asymmetric borane reductions is not very sensitive to stereoelectronic effects.

The sigmatropic 1,3-rearrangement (hydride shift) of the compound (IIIa) or (IIIb) to a compound of formula (IVa) or (IVb) may be carried out by treatment with a base, such as triethylamine, and a palladium catalyst, such as Pd(dppe)Cl$_2$ ([1,2-bis(diphenylphosphino)ethane]palladium (II) chloride) in an organic solvent (see e.g. the above WO 97/17341). Alternatively, the rearrangement reaction may be carried out by treatment with DABCO (1,4-diazabicyclo [2.2.2]octane) and a base, such as triethylamine, in an organic solvent (see Example 1 below). The indanone (IVa) or (IVb) obtained is generally a highly crystalline solid which makes it possible to raise the enantiomeric purity, if desired, by recrystallization from a suitable solvent (for example, an enantiomeric excess (as defined below) of 99% or more may be obtained).

The Baeyer-Villiger oxidation of compounds (IVa) and (IVb) may be performed by a variety of oxidizing agents as is well known in the art, e.g. hydrogen peroxide or a peroxy acid, such as 3-chloro-peroxybenzoic acid, preferably in the presence of an acid catalyst, such as p-tolylsulphonic acid (TsOH). The reaction is preferably carried out in an organic solvent and at e.g. from about 0° C. to about room temperature.

Enantiomeric purity, or enantiomeric enrichment, is usually expressed as "enantiomeric excess", below abbreviated as "ee", and defined as $(R-S)/(R+S)$, where R and S are the amounts of the R- and S-enantiomers, respectively. For the purposes of the present invention, the enantiomeric purity in the enantioselective process steps is usually at least about 50%, preferably at least about 85%.

Since tolterodine is an amine, it may form salts with both organic and inorganic acids. The pharmaceutically acceptable salts may, depending on the pharmaceutical formulation, be preferred over the corresponding free amines since they produce compounds which are more water soluble and more crystalline. Exemplary pharmaceutically acceptable salts include salts with acids such as methane sulphonic, hydrochloric, hydrobromic, sulphuric, phosphoric, nitric, benzoic, citric, tartaric, fumaric, and maleic acids.

The invention will now be illustrated further by the following non-limiting Example.

In the Example:

TLC refers to thin-layer chromatography.

MeCBS refers to 3,3-diphenyl-1-methyltetrahydro-1H, 3H-pyrrolo-[1,2-c][1.3.2]oxazaborole.

DABCO refers to 1,4-diazabicyclo[2.2.2]octane.

ChiralCel OD-H (trademark) refers to a chiral stationary phase for liquid chromatography consisting of cellulose tris(3,5-dimethylphenyl carbamate) on a silica gel substrate (Daicel Chemical Industries, Ltd).

mCPBA refers to 3-chloroperoxybenzoic acid.

"ee" refers to enantiomeric excess as defined above.

EXAMPLE 1

1-(2-Bromo-4-methyl-phenyl)-3-phenyl-propenone

To a solution of 2-bromo-4-methylacetophenone (7.20 g, 34.0 mmol) and benzaldehyde (3.65 g, 34.0 mmol) in dry methanol (50 ml) was added freshly prepared sodium methoxide (35.7 mmol) in dry methanol (30 ml) at 0° C. The resulting mixture was stirred at 0° C. for 5 h and raised to room temperature over night. 10 ml of HCl (10%) were added slowly and the mixture was evaporated to near dryness under reduced pressure. The residue was suspended in saturated NaHCO$_3$ (50 ml) and extracted with 3×50 ml diethyl ether, washed with brine and dried over MgSO$_4$. Purification by flash chromatography eluting with diethyl ether:pentane 5:95, gave 10.1 g (95%) of the title compound. $R_f$ 0.66 (diethyl ether:pentane 20:80). $^1$H NMR δ: 2.25 (s, 3H), 6.96 (d, J=10.2 Hz, 1H), 7.15 (d, J=10.2 Hz, 1H), 7.05 (dd, J=7.6 Hz, 2.6 Hz, 1H), 7.24 (m, 3H), 7.34 (m, 2H), 7.40 (m, 3H). $^{13}$C NMR δ: 21.4, 112.5, 117.3, 122.5, 122.8, 123.7, 124.9, 128.4, 132.2, 133.6, 133.9, 143.6, 145.3, 186.6.

5-Methyl-3-phenyl-inden-1-one

To a suspension of anhydrous $K_2CO_3$ (9.76 g, 70.6 mmol) in dry DMF (100 ml) was added 1-(2-bromo-4-methyl-phenyl)-3-phenyl-propenone (8.40 g, 28.3 mmol), and the mixture was deaerated with dry argon for 15 min. Triphenylphosphine (0.73 g, 2.83 mmol) was added followed by $PdCl_2$ (0.20 g, 1.13 mmol). The mixture was heated at 80° C. until NMR sample indicated disappearance of starting material (5 h). The mixture was reduced to half volume under reduced pressure and poured on ice:water (200 ml). Extractive work-up with $CH_2Cl_2$ followed by flash chromatography eluting with diethyl ether:pentane 5:95 gave 4.2 g (72%) of the title compound. $R_f$ 0.62 (diethyl ether:pentane 20:80). IR (neat cm$^{-1}$): 1704, 1606, 1355, 1101, 815, 743. $^1$H NMR δ: 2.40 (s, 3H), 5.99 (s, 1H), 7.11 (d, J=7.2 Hz, 1H), 7.18 (s, 1H), 7.43 (d, J=7.6 Hz, 1H), 7.53 (m, 3H), 7.66 (m, 2H). $^{13}$C NMR δ: 22.1, 122.7, 122.9, 123.5, 127.4, 128.6, 128.9, 129.2, 129.9, 130.3, 133.2, 143.7, 144.4, 162.4. MS (EI 70 eV) m/z (rel. intensity): 220 (100) [M$^+$], 205 (75), 191 (51), 177 (10), 165 (15).

5-Methyl-3-phenyl-(S)-1H-inden-1-ol (R)-MeCBS catalyst (0.22 ml, 1 M, 0.22 mmol) was mixed in 5 ml of dry THF, and stirred for 1 h at room temperature. After cooling to 0° C., 2.5 ml of 2 M $BH_3$:Me$_2$S (4.99 mmol) in THF were added. 5-Methyl-3-phenyl-inden-1-one (1.00 g, 4.54 mmol) was added as a solution in toulene (2 ml) over 2 h via a syringe pump. The reaction was followed by TLC. After completeness, methanol (0.6 ml, 17 mmol) was added at 0° C. and the mixture was evaporated to dryness. Flash chromatography eluting with ethyl acetate:pentane 10:90 gave 0.96 g (95%) of the title compound. $R_f$ 0.35 (ethyl acetate:pentane 20:80) (ChiralCel OD-H) 0.5 ml/min of hexane/isopropanol: 95/5 (S)-isomer 24.53 min, (R)-isomer 27.22 min, 93% ee. IR (neat cm$^{-1}$): 3300, 1605, 1446, 949, 813. $^1$H NMR δ: 1.40 (s, 1H), 2.40 (s, 3H), 5.27 (d, J=8 Hz, 1H), 6.43 (d J=2 Hz, 1H), 7.18 (d, J=8 Hz, 1H), 7.27 (s, 1H), 7.47 (m, 4H), 7.59 (m, 2H). $^{13}$C NMR δ: 21.6, 76.2, 121.6, 123.6, 126.9, 127.6, 128.2, 128.6, 134.1, 134.9, 138.2, 142.1, 143.7, 145.6. MS (EI 70 eV) m/z (rel. intensity): 220 (100) [M$^+$], 207 (71), 178 (66), 144 (42), 116 (23).

5-Methyl-3-(S)-phenyl-indan-1-one

5-Methyl-3-phenyl-(S)-1H-inden-1-ol (750 mg, 3.41 mmol) and DABCO (190 mg, 1.71 mmol) were dissolved in dry THF:triethylamine 20:1 (15 ml) and refluxed for 3 h. The reaction mixture was evaporated to dryness. Flash chromatography eluting with ethyl acetate:pentane 5:95 gave 690 mg (92%) of the title compound. $R_f$ 0.62 (ethyl actetate:pentane 20:80) (ChiralCel OD-H) 0.5 ml/min of hexane/isopropanol: 95/5 (S)-isomer 19.12 min, (R)-isomer 22.33 min, 89% ee. IR (neat cm$^{-1}$): 3027, 2361, 1710, 1605, 1280, 1238, 1040. $^1$H NMR δ: 2.39 (s, 3H), 2.69 (dd, J=3.0, 19.2 Hz, 1H), 3.23 (dd, J=8.0, 19.2 Hz, 1H), 4.53 (q, J=4 Hz, 1H), 7.07 (s, 1H), 7.14 (d, J=8.4 Hz, 1H), 7.15 (s, 1H), 7.26 (m, 2H), 7.33 (m, 2H), 7.72 (d, J=7.6 Hz, 1H). $^{13}$C NMR δ: 22.1, 44.3, 46.9, 123.2, 126.9, 127.0, 127.6, 128.9, 134.5, 143.8, 146.3, 158.4, 205.5. MS (EI 70 eV) m/z (rel. intensity): 220 (100) [M$^+$], 207 (55), 194 (19), 178 (60), 144 (10).

6-Methyl-4-(S)-phenyl-chroman-2-one

5-Methyl-3-(S)-phenyl-indan-1-one (400 mg, 1.8 mmol) and mCPBA (98%, 485 mg, 2.8 mmol) were suspended in dry $CH_2Cl_2$ (6 ml) at 0° C. followed by TsOH:H$_2$O (20 mg). The reaction was kept at 4° C. for 48 h. The mixture was diluted with 10 ml of $CH_2Cl_2$ and washed with 2×10 ml of saturated $Na_2SO_3$, saturated $NaHCO_3$ and brine. Flash chromatography eluting with ethyl acetate:pentane 10:90 gave 390 mg (90%) of the title compound. $R_f$ 0.83 (ethyl acetate:pentane 20:80) (ChiralCel OD-H) 0.5 mL/min of hexane/isopropanol 95/5 (S)-isomer 15.18 min, (R)-isomer 17.42 min, 89% ee. IR (neat cm$^{-1}$): 2900, 2360, 1769, 1495, 1208, 1145. $^1$H NMR δ: 2.28 (s, 3H), 3.05 (m, 1H), 4.32 (t, J=6.8 Hz, 1H), 6.98 (s, 1H), 7.04 (d, J=8.4 Hz, 1H), 7.11 (dd, J=2.0, 8.4 Hz, 1H), 7.18 (d, J=8.4 Hz, 1H), 7.19 (s, 1H), 7.33 (m, 3H) $^{13}$C NMR δ: 20.7 37.1, 40.7, 116.8, 125.3, 127.5, 127.6, 128.6, 129.1, 129.3, 134.3, 140.5, 149.6, 167.8. MS (EI 70 eV) m/z (rel. intensity): 238 (55) [M$^+$], 220 (57), 195 (100), 181(10), 165 (12), 152 (9).

(R)-N,N-diisopropyl-3(2-hydroxy-5-methylphenyl)-3-phenylpropanamine (tolterodine)

Tolterodine may be prepared from 6-methyl-4-(S)-phenyl-chroman-2-one as obtained above by method steps corresponding to Examples 3 and 4 of the above-mentioned U.S. Pat. No. 5,929,914 (the full disclosure of which is incorporated by reference herein), i.e. by (i) reducing the lactone 6-methyl-4-(S)-phenyl-chroman-2-one with diisobutylaluminiumhydride in toluene solution at −20 to −25° C. to the corresponding hydroxy compound, 6-methyl-4-(S)-phenyl-chroman-2-ol; (ii) reductively aminating the 6-methyl-4-(S)-phenyl-chroman-2-ol in methanol by reaction with diisopropylamine and hydrogenation with palladium on carbon at 45–50 psi and 48° C., and subsequent filtration (solka floc) to obtain the title compound (tolterodine) in substantially enantiomerically pure form.

What is claimed is:

1. A compound of the formula:

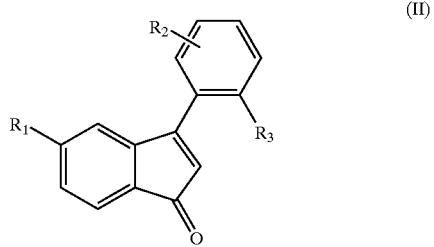

(II)

wherein $R_1$ is methyl or hydroxymethyl and $R_2$ and $R_3$ are hydrogen, or a salt thereof.

2. The compound of claim 1, wherein $R_1$ is methyl.

3. The compound of claim 1, wherein $R_1$ is hydroxymethyl.

4. The compound of claim 1, wherein the compound is a salt of the compound of formula (II).

* * * * *